United States Patent
Akagane

(10) Patent No.: US 9,199,099 B2
(45) Date of Patent: Dec. 1, 2015

(54) ULTRASONIC TRANSMITTING UNIT AND MANUFACTURING METHOD OF ULTRASONIC TRANSMITTING UNIT

(71) Applicant: OLYMPUS CORPORATION, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/319,036

(22) Filed: Jun. 30, 2014

(65) Prior Publication Data
US 2015/0018726 A1  Jan. 15, 2015

Related U.S. Application Data

(63) Continuation of application No. PCT/JP2013/078110, filed on Oct. 16, 2013.

(60) Provisional application No. 61/716,947, filed on Oct. 22, 2012.

(51) Int. Cl.
*A61B 8/00* (2006.01)
*A61N 7/00* (2006.01)
(Continued)

(52) U.S. Cl.
CPC .......... *A61N 7/00* (2013.01); *A61B 17/320068* (2013.01); *H04R 31/00* (2013.01); *A61B 2017/00477* (2013.01); *A61B 2017/00526* (2013.01); *A61B 2017/320088* (2013.01); *Y10T 29/49005* (2015.01)

(58) Field of Classification Search
CPC ..................... A61B 17/320068; A61B 18/148; A61B 17/320092; A61B 18/1442; A61B 8/00; A61B 17/32; A61B 18/14
See application file for complete search history.

(56) References Cited

U.S. PATENT DOCUMENTS 5,391,144 A  2/1995  Sakurai et al.
6,328,703 B1  12/2001  Murakami
(Continued)

FOREIGN PATENT DOCUMENTS

JP  A-1-171537  7/1989
JP  A-2001-8943  1/2001
(Continued)

OTHER PUBLICATIONS

May 7, 2015 International Preliminary Report on Patentability issued in International Application No. PCT/JP2013/078110.
(Continued)

*Primary Examiner* — Joel Lamprecht
(74) *Attorney, Agent, or Firm* — Oliff PLC

(57) ABSTRACT

A distal side transmitting member of an ultrasonic transmitting unit includes a projecting portion protruding from a distal side abutment portion toward a proximal direction, and a proximal side transmitting member includes a depressed portion depressed from a proximal side abutment portion toward the proximal direction. A cavity portion having a space is formed between a protruding end of the projecting portion and a bottom portion of the depressed portion inside the proximal side transmitting member when the depressed portion is engaged with the projecting portion, and one of anti-node positions of an ultrasonic vibration is located within a range from the protruding end to the bottom portion.

9 Claims, 9 Drawing Sheets

(51) Int. Cl.
*A61B 17/32* (2006.01)
*H04R 31/00* (2006.01)
*A61B 17/00* (2006.01)

(56) References Cited

U.S. PATENT DOCUMENTS

| 8,956,375 | B2 * | 2/2015 | Nita | A61B 17/22 |
| | | | | 606/169 |
| 2001/0001123 | A1 | 5/2001 | Madan et al. | |
| 2003/0225332 | A1 | 12/2003 | Okada et al. | |
| 2008/0294051 | A1 | 11/2008 | Koshigoe et al. | |

FOREIGN PATENT DOCUMENTS

| JP | A-2002-542690 | 12/2002 |
| JP | A-2008-289876 | 12/2008 |

OTHER PUBLICATIONS

International Search Report issued in International Patent Application No. PCT/JP2013/078110 dated Nov. 12, 2013 (with translation).

* cited by examiner

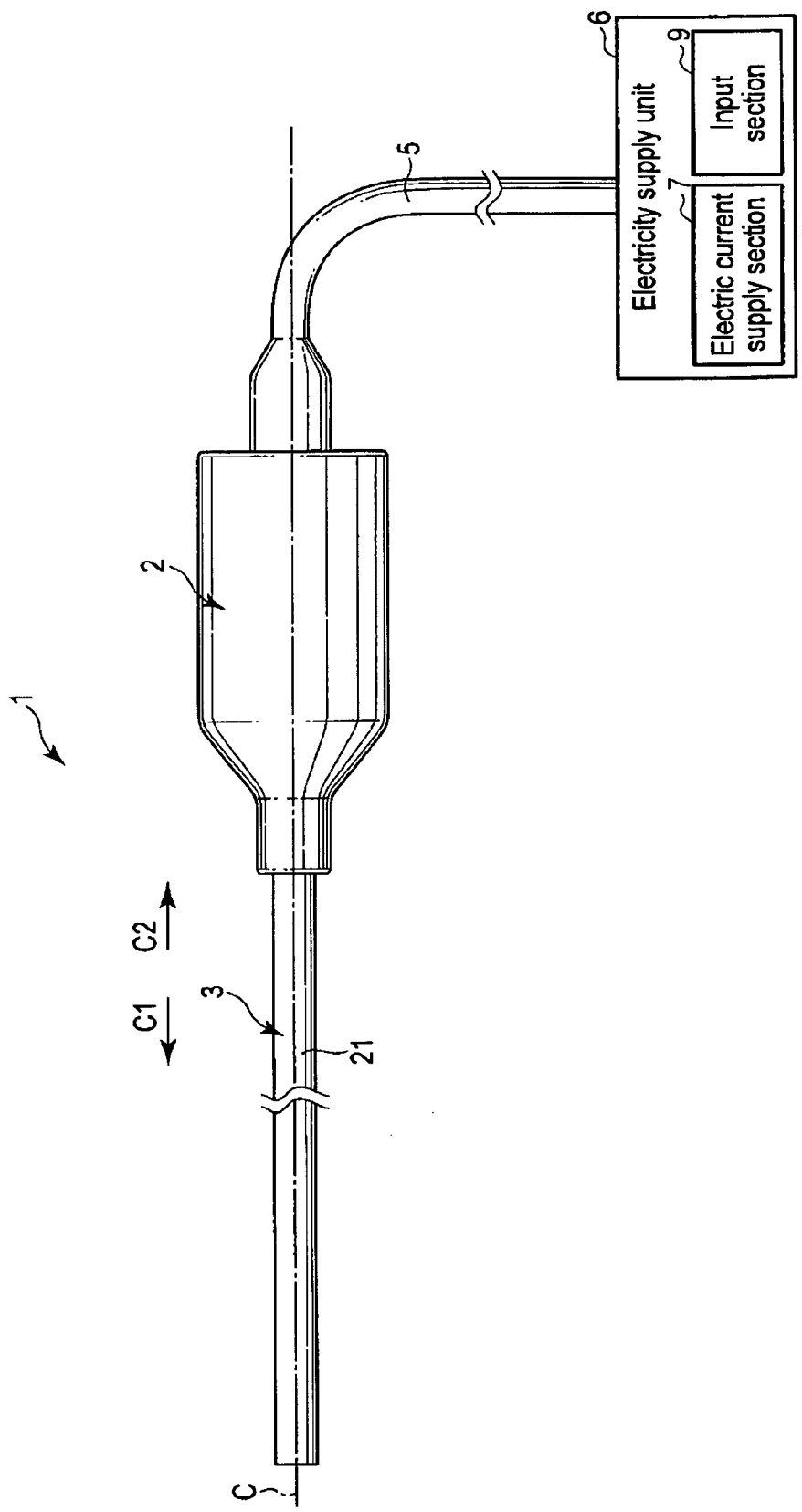
F I G. 1

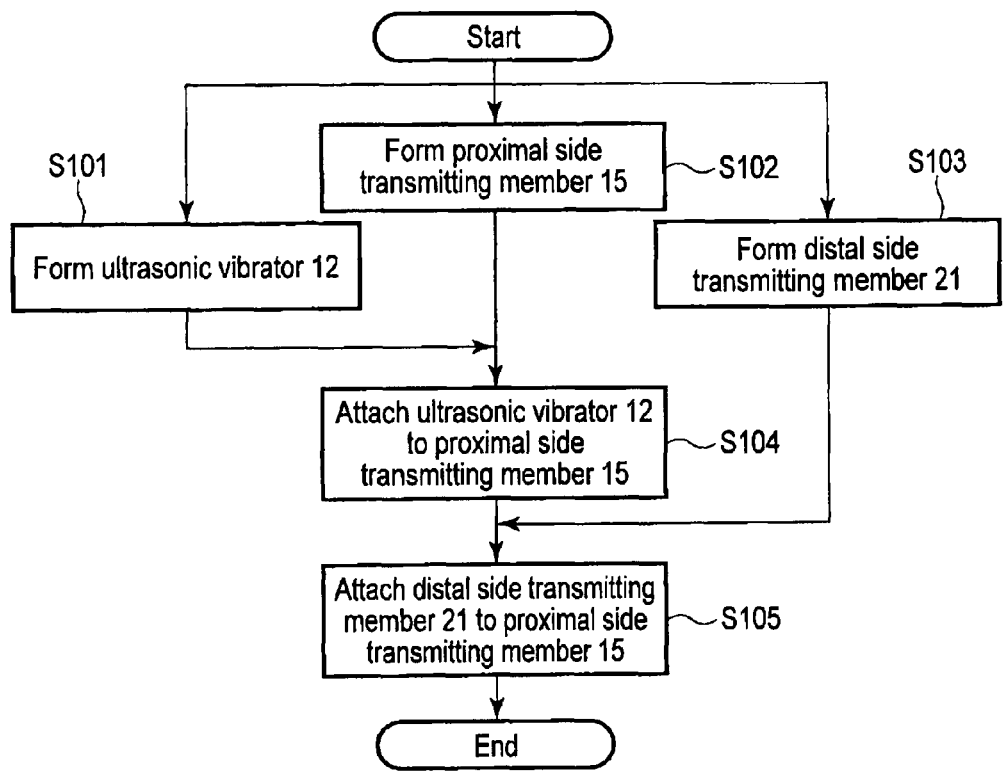
F I G. 5
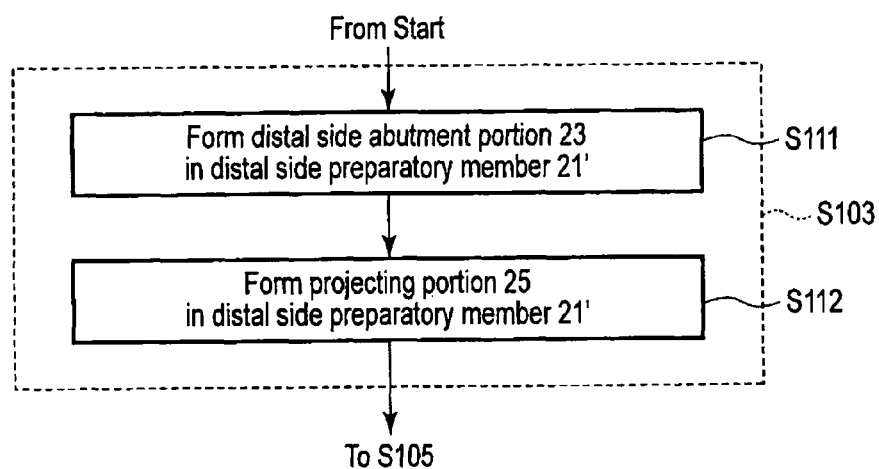
F I G. 6

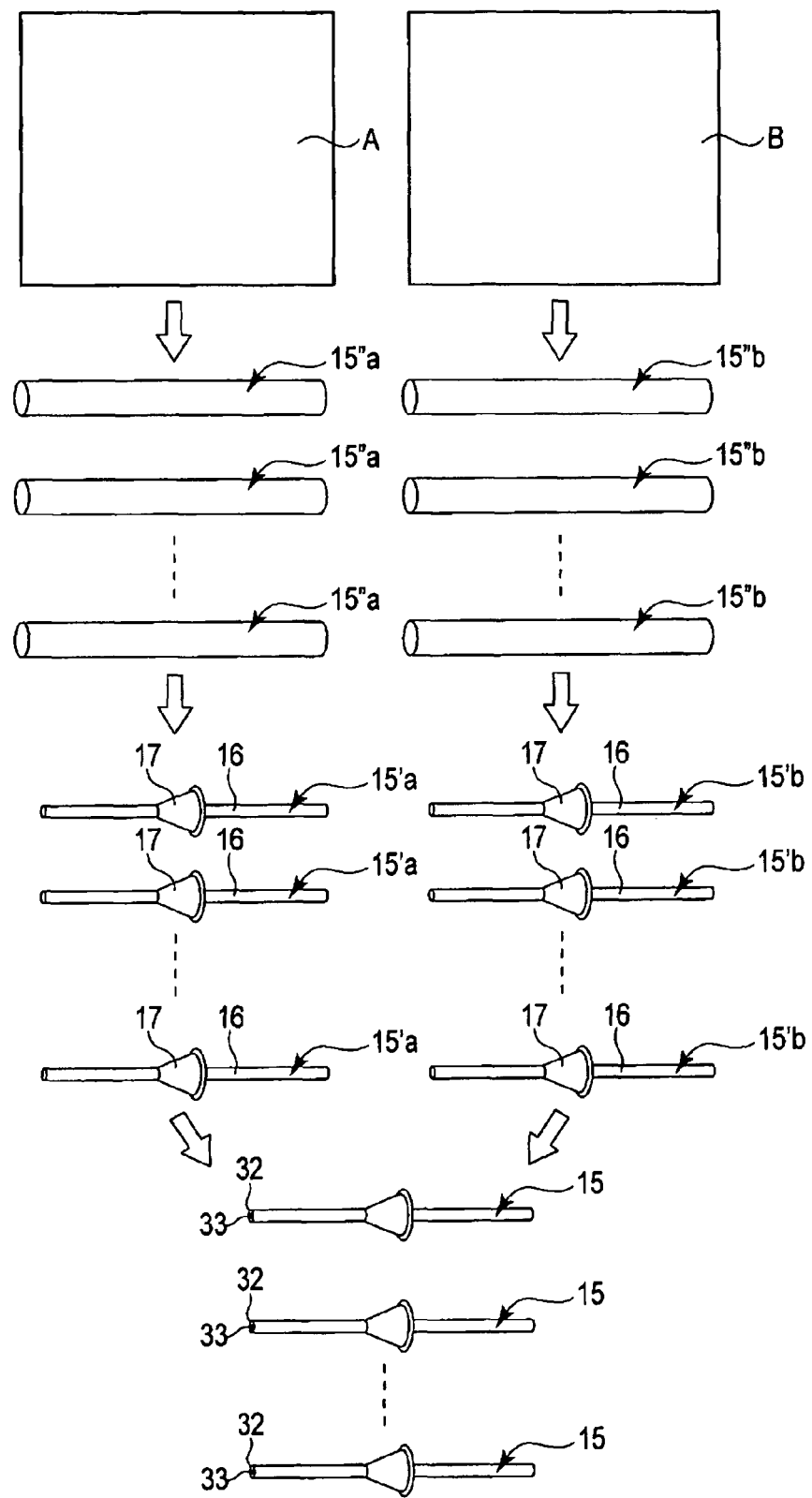
F I G. 9

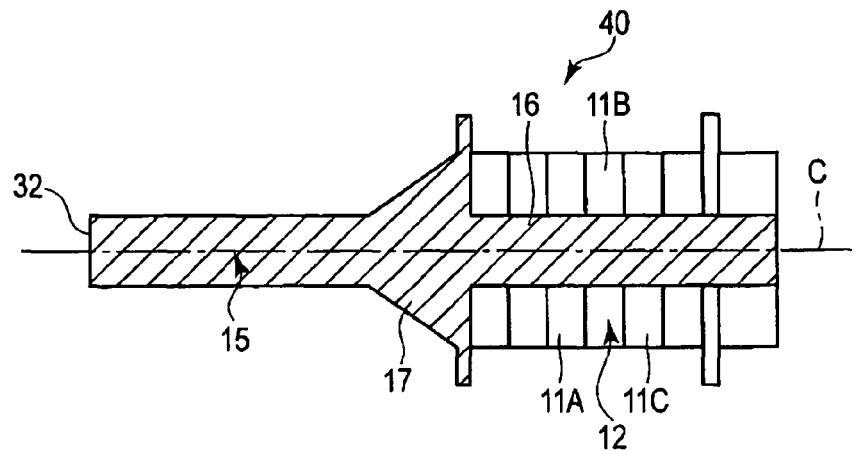
F I G. 10A
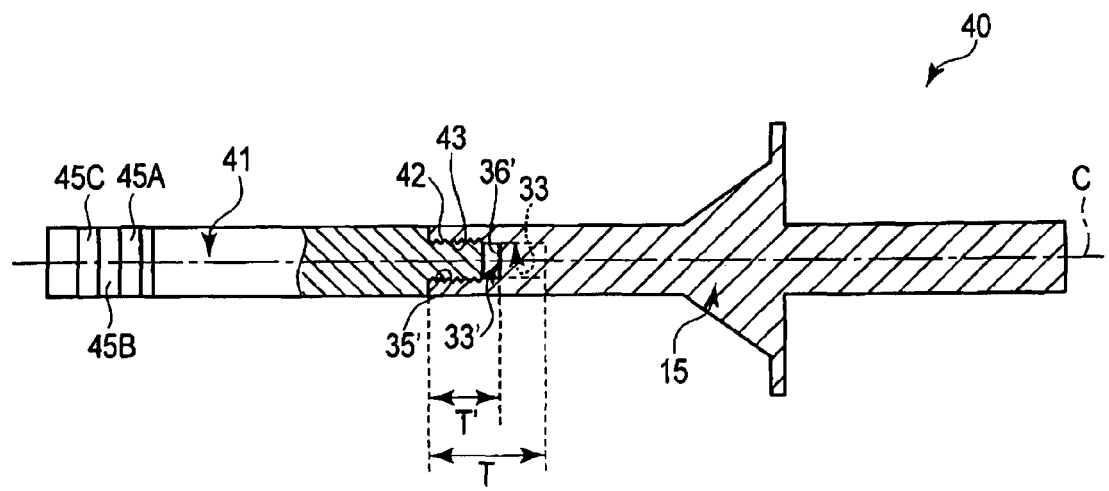
F I G. 10B

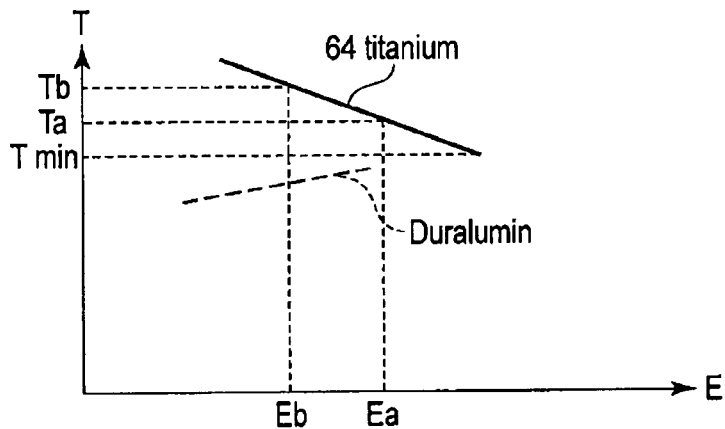
F I G. 11
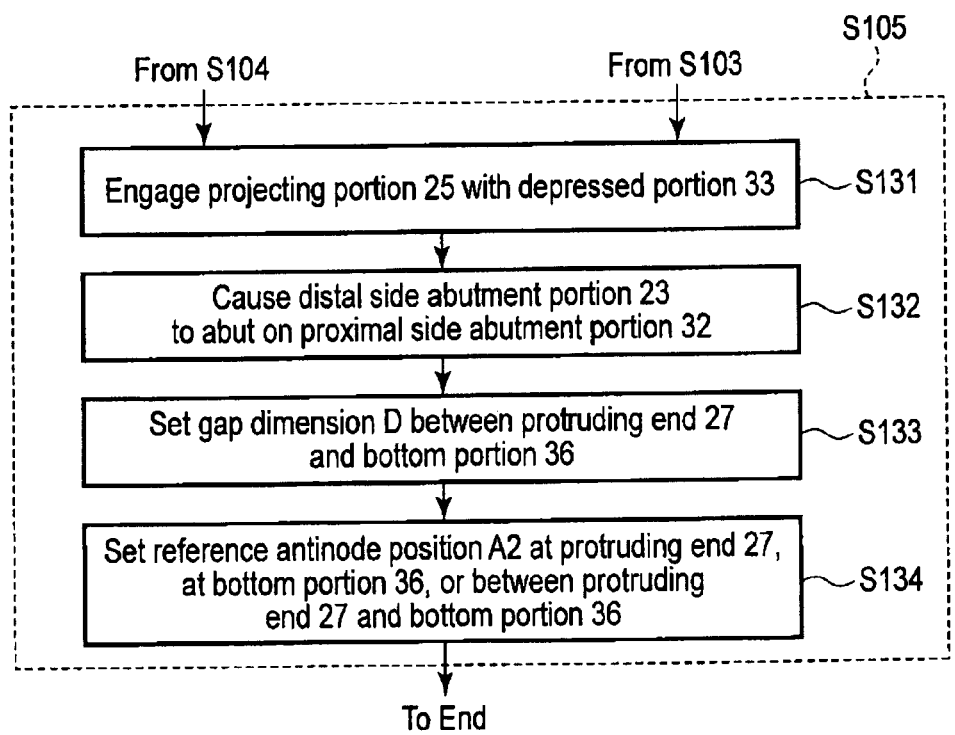
F I G. 12

ULTRASONIC TRANSMITTING UNIT AND MANUFACTURING METHOD OF ULTRASONIC TRANSMITTING UNIT

CROSS-REFERENCE TO RELATED APPLICATIONS

This is a Continuation Application of PCT Application No. PCT/JP2013/078110, filed Oct. 16, 2013 and based upon and claiming the benefit of priority from prior U.S. Provisional Application No. 61/716,947, filed Oct. 22, 2012, the entire contents of which are incorporated herein by reference.

BACKGROUND OF THE INVENTION

1. Field of the Invention

The present invention relates to an ultrasonic transmitting unit which extends along a longitudinal axis and which can transmit an ultrasonic vibration from a proximal direction toward a distal direction. The present invention also relates to a manufacturing method of an ultrasonic transmitting unit.

2. Description of the Related Art

Ultrasonic treatment devices including ultrasonic transmitting units are disclosed in the specification of U.S. Patent Application Publication No. 2003/225332 and the specification of U.S. Pat. No. 5,391,144. Each of the ultrasonic transmitting units is provided with a vibration generating portion such as an ultrasonic vibrator which is configured to generate an ultrasonic vibration, a proximal side transmitting member to which the vibration generating portion is attached, and a distal side transmitting member (ultrasonic probe) which is attached to the proximal side transmitting member. The ultrasonic vibration generated in the vibration generating portion is transmitted to the proximal side transmitting member from the vibration generating portion, and transmitted to the distal side transmitting member from the proximal side transmitting member. That is, the ultrasonic vibration is transmitted from a proximal direction toward a distal direction. A horn which is configured to increase the amplitude of the ultrasonic vibration is provided in the proximal side transmitting member. An internal thread portion is formed in the proximal side transmitting member from a distal end thereof toward the proximal direction. An external thread portion is formed in the distal side transmitting member from a proximal end thereof toward the distal direction. The external thread portion is screwed to the internal thread portion, and the distal side transmitting member is thereby attached to the proximal side transmitting member.

BRIEF SUMMARY OF THE INVENTION

According to one aspect of the invention, an ultrasonic transmitting unit which extends along a longitudinal axis and which is configured to transmit an ultrasonic vibration from a proximal direction toward a distal direction and thereby configured to vibrate at a predetermined resonance frequency, the ultrasonic transmitting unit including: a vibration generating portion which is configured to generate the ultrasonic vibration; a proximal side transmitting member to which the vibration generating portion is attached and to which the ultrasonic vibration is configure to be transmitted from the vibration generating portion, the proximal side transmitting member including a proximal side abutment portion which forms a distal end of the proximal side transmitting member; a distal side transmitting member which is connected to the distal direction side of the proximal side transmitting member and to which the ultrasonic vibration transmitted to the proximal side transmitting member from the vibration generating portion is configured to be transmitted, the distal side transmitting member including a distal side abutment portion on which the proximal side abutment portion of the proximal side transmitting member abuts when the distal side transmitting member is connected to the proximal side transmitting member; a projecting portion protruding from the distal side abutment portion toward the proximal direction in the distal side transmitting member, the projecting portion including a protruding end located a predetermined protruding dimension apart from the distal side abutment portion toward the proximal direction; and a depressed portion which is depressed from the proximal side abutment portion toward the proximal direction and which includes a bottom portion depressed a predetermined depression dimension equal to or more than the predetermined protruding dimension apart from the proximal side transmitting member toward the proximal direction, the depressed portion forming a cavity portion having a space between the protruding end of the projecting portion and the bottom portion of the depressed portion inside the proximal side transmitting member when the distal side transmitting member is connected to the proximal side transmitting member and then the depressed portion is engaged with the projecting portion, one of antinode positions of the ultrasonic vibration being located within a range from the protruding end of the projecting portion to the bottom portion of the depressed portion in a situation in which the ultrasonic transmitting unit vibrates at the predetermined resonance frequency.

According to one another aspect of the invention, a manufacturing method of an ultrasonic transmitting unit which extends along a longitudinal axis and which is configured to transmit an ultrasonic vibration from a proximal direction toward a distal direction and thereby configured to vibrate at a predetermined resonance frequency, the manufacturing method including: forming a vibration generating portion which is configure to generate the ultrasonic vibration; forming a proximal side transmitting member to which the ultrasonic vibration is configured to be transmitted from the vibration generating portion and forming a distal end of the proximal side transmitting member by a proximal side abutment portion; attaching the vibration generating portion to the proximal side transmitting member; forming a distal side transmitting member to which the ultrasonic vibration is configured to be transmitted from the proximal side transmitting member; connecting the distal side transmitting member to the distal direction side of the proximal side transmitting member so that the proximal side abutment portion of the proximal side transmitting member abuts on a distal side abutment portion of the distal side transmitting member; forming a projecting portion protruding from the distal side abutment portion toward the proximal direction in the distal side transmitting member, and forming a proximal end of the distal side transmitting member by a protruding end of the projecting portion which is located a predetermined protruding dimension apart from the distal side abutment portion toward the proximal direction; forming a depressed portion which is depressed from the proximal side abutment portion toward the proximal direction in the proximal side transmitting member, and forming a bottom portion of the depressed portion a predetermined depression dimension equal to or more than the predetermined protruding dimension apart from the proximal side transmitting member toward the proximal direction; forming a cavity portion having a space between the protruding end of the projecting portion and the bottom portion of the depressed portion inside the proximal side transmitting member when the distal side transmitting member is connected to the proximal side transmitting member and then the depressed portion is engaged with the projecting portion; and connecting the distal side transmitting member to the proximal side transmitting member so that one of antinode positions of the ultrasonic vibration is located within a range from the protruding end of the projecting portion to the bottom portion of the depressed portion when the ultrasonic transmitting unit vibrates at the predetermined resonance frequency.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing an ultrasonic treatment device according to a first embodiment of the present invention;

FIG. 5 is a flowchart showing a manufacturing method of the ultrasonic transmitting unit according to the first embodiment;

FIG. 6 is a flowchart showing a method of forming a distal side transmitting member according to the first embodiment;

FIG. 9 is a schematic diagram illustrating the method of forming the proximal side transmitting member according to the first embodiment;

FIG. 10A is a schematic diagram showing a temporary vibration unit according to a certain example of the first embodiment;

FIG. 10B is a schematic diagram showing a temporary vibration unit according to another certain example of the first embodiment;

FIG. 11 is a schematic diagram showing the relation between the Young's modulus of the proximal side transmitting member and a depression dimension of a depressed portion in a situation in which the ultrasonic transmitting unit according to the first embodiment vibrates at a predetermined resonance frequency;

FIG. 12 is a flowchart showing a method of attaching the distal side transmitting member to the proximal side transmitting member according to the first embodiment;

DETAILED DESCRIPTION OF THE INVENTION

First Embodiment

Figure 2:
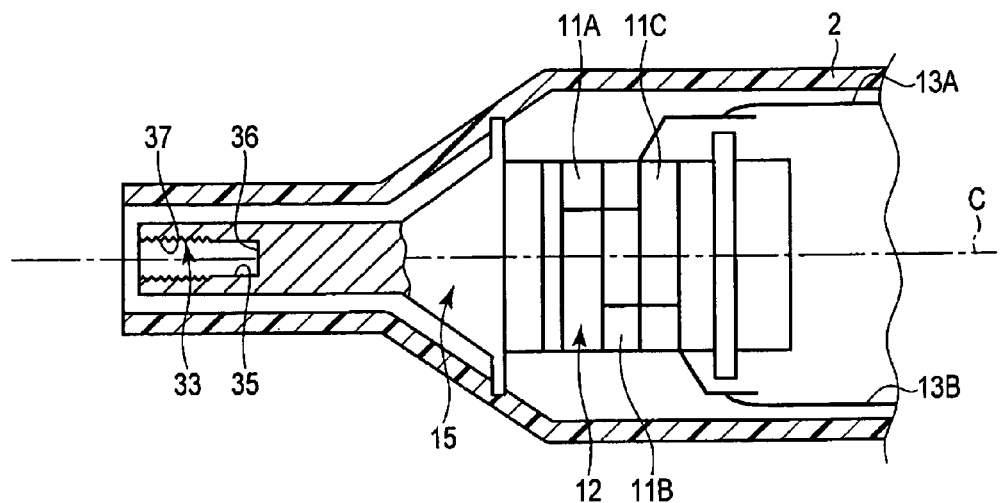
FIG. 2 is a sectional view schematically showing the internal configuration of a vibrator case according to the first embodiment.

A first embodiment of the present invention is described with reference to FIG. 1 to FIG. 12. FIG. 1 is a diagram showing an ultrasonic treatment device 1 according to the present embodiment. As shown in FIG. 1, the ultrasonic treatment device 1 has a longitudinal axis C. Here, one of two directions parallel to the longitudinal axis C is a distal direction (direction of an arrow C1 in FIG. 1), and the direction opposite to the distal direction is a proximal direction (direction of an arrow C2 in FIG. 1). The ultrasonic treatment device 1 includes a vibrator case 2, and an ultrasonic transmitting unit 3 extending from an inside of the vibrator case 2 toward the distal direction along the longitudinal axis C.

One end of a cable 5 is connected to a proximal end of the oscillator case 2. The other end of the cable 5 is connected to an electricity supply unit 6. The electricity supply unit 6 includes an electric current supply section 7 and an input section 9.

Figure 3:
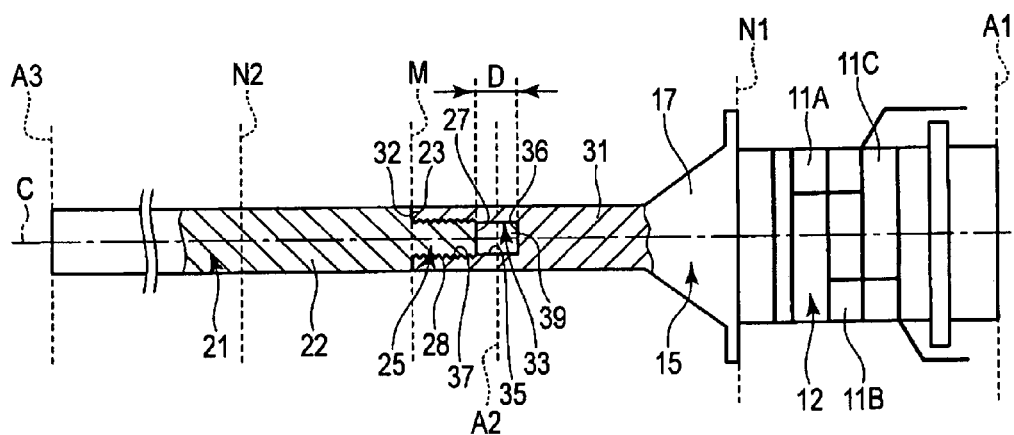
FIG. 3 is a schematic diagram showing the configuration of an ultrasonic transmitting unit according to the first embodiment.
Figure 4:
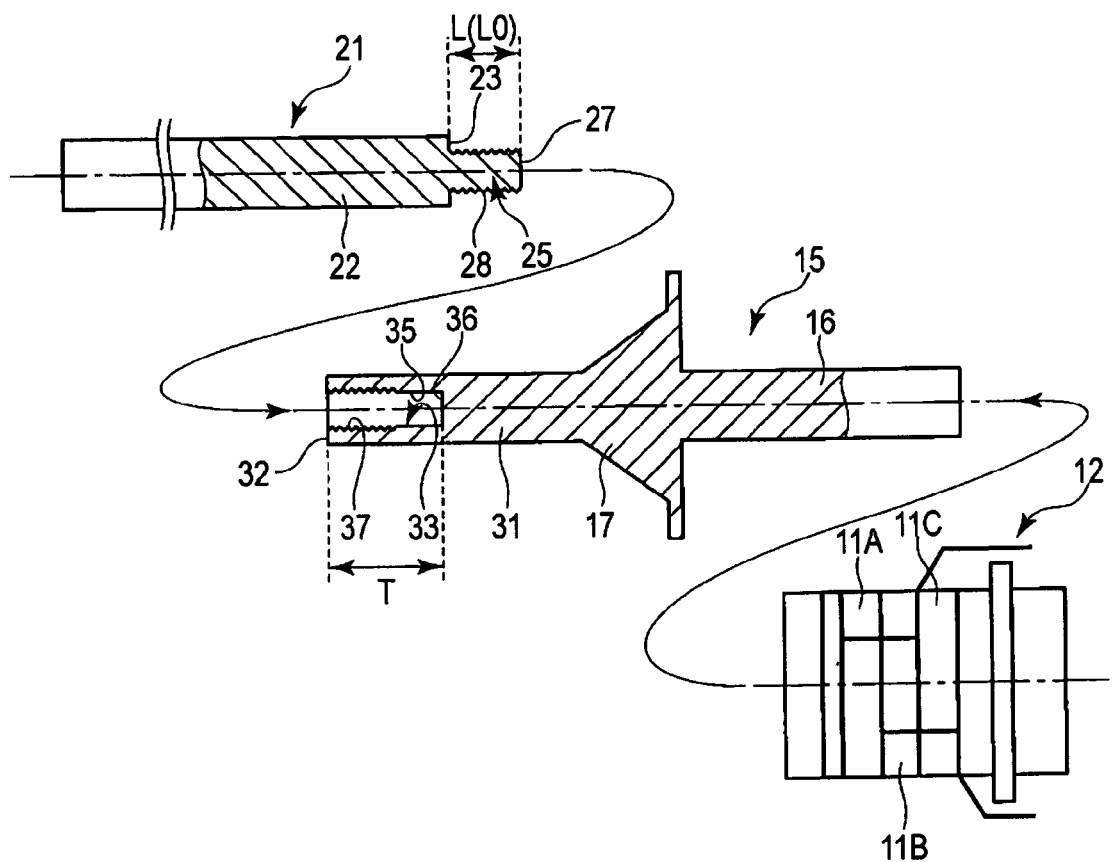
FIG. 4 is a schematic diagram showing the configuration of the ultrasonic transmitting unit according to the first embodiment that is disassembled into components.

FIG. 2 is a diagram showing the internal configuration of the vibrator case 2. FIG. 3 and FIG. 4 are diagrams showing the configuration of the ultrasonic transmitting unit 3. As shown in FIG. 2 to FIG. 4, the ultrasonic transmitting unit 3 is provided with an ultrasonic vibrator 12 which is a vibration generating portion including piezoelectric elements 11A to 11C which are configured to convert an electric current to an ultrasonic vibration. The ultrasonic oscillator 12 is provided inside the vibrator case 2. One end of each of electric wiring lines 13A and 13B is connected to the ultrasonic vibrator 12. Each of the electric wiring lines 13A and 13B has the other end connected to the electric current supply section 7 of the electricity supply unit 6 through the cable 5. The ultrasonic vibration is generated in the ultrasonic vibrator 12 by the supply of an electric current to the ultrasonic vibrator 12 from the electric current supply section 7 via the electric wiring lines 13A and 13B.

The ultrasonic transmitting unit 3 includes a proximal side transmitting member 15 to which the ultrasonic vibration is transmitted from the ultrasonic vibrator 12. The proximal side transmitting member 15 includes a rod portion 16 to which the ultrasonic vibrator 12 is attached, and a horn 17 continuous with the distal direction side of the rod portion 16. The ultrasonic vibrator 12 including the piezoelectric elements 11A to 11C and other parts is inserted through the rod portion 16. The inserted ultrasonic oscillator 12 is fixed to the rod portion 16. As a result, the ultrasonic vibrator 12 is attached to the proximal side transmitting member 15. The horn 17 is attached to the oscillator case 2. The amplitude of the ultrasonic vibration is increased by the horn 17.

The ultrasonic transmitting unit 3 includes a distal side transmitting member 21 to which the ultrasonic vibration is transmitted from the proximal side transmitting member 15. The distal side transmitting member 21 is, for example, an ultrasonic probe. The distal side transmitting member 21 is attached to the distal direction side of the proximal side transmitting member 15. The ultrasonic vibration generated in the ultrasonic vibrator 12 is transmitted up to a distal end of the distal side transmitting member 21 from the proximal direction toward the distal direction. The ultrasonic vibration is a longitudinal vibration having a vibration direction and a transmission direction that are parallel to the longitudinal axis C.

The ultrasonic transmitting unit 3 has antinode positions (e.g., A1 to A3) and node positions (e.g., N1 and N2) of the ultrasonic vibration. The antinode position A1 is located at the proximal end of the ultrasonic transmitting unit 3 (the proximal end of the ultrasonic vibrator 12). The antinode position A3 is located at the distal end of the ultrasonic transmitting unit 3 (the distal end of the distal side transmitting member 21). Therefore, the dimension of the ultrasonic transmitting unit 3 in directions parallel to the longitudinal axis C is a dimension equal to an integral multiple of a half wavelength of the ultrasonic vibration. Thus, when the ultrasonic vibration is transmitted from the proximal direction toward the distal direction, the ultrasonic transmitting unit 3 vibrates at a predetermined resonance frequency f0.

The distal side transmitting member 21 includes a distal side member body 22, and a distal side abutment portion 23 provided at a proximal end of the distal side member body 22. The distal side abutment portion 23 is formed into a flat shape perpendicular to the longitudinal axis C. The distal side abutment portion 23 is located at a midway position M different from the loop positions (A1 to A3) and the node positions (N1 and N2) of the ultrasonic vibration when the distal side transmitting member 21 and the proximal side transmitting member 15 are connected to each other.

The distal side transmitting member 21 includes a projecting portion 25 protruding from the distal side abutment portion 23 toward the proximal direction. The projecting portion 25 includes a protruding end 27 located at the proximal end of the distal side transmitting member 21. The protruding end 27 is located a protruding dimension L apart from the distal side abutment portion 23 in the proximal direction. An external thread portion 28 is provided on the outer peripheral portion of the projecting portion 25.

The proximal side transmitting member 15 includes a proximal side member body 31, and a proximal side abutment portion 32 which abuts on the distal side abutment portion 23. The proximal side abutment portion 32 is provided at a distal end of the proximal side transmitting member 15 (the distal end of the proximal side member body 31), and is formed into a flat shape perpendicular to the longitudinal axis C. When the distal side transmitting member 21 and the proximal side transmitting member 15 are connected to each other, the proximal side abutment portion 32 abuts on the distal side abutment portion 23, and is therefore located at the midway position M different from the antinode positions (A1 to A3) and the node positions (N1 and N2) of the ultrasonic vibration. The ultrasonic vibration is transmitted to the distal side transmitting member 21 from the proximal side transmitting member 15 via the proximal side abutment portion 32 and the distal side abutment portion 23.

The proximal side transmitting member 15 includes a depressed portion 33 depressed from the proximal side abutment portion 32 in the proximal direction. The depressed portion 33 includes a side portion 35 and a bottom portion 36. An internal thread portion 37 is formed on the side portion 35 of the concave portion 33. The external thread portion 28 of the projecting portion 25 is screwed to the internal thread portion 37, and the projecting portion 25 is thereby engaged with the depressed portion 33. As a result, the distal side transmitting member 21 is attached to the proximal side transmitting member 15.

The bottom portion 36 of the depressed portion 33 is located a depression dimension T equal to or more than the protruding dimension L of the projecting portion 25 apart from the proximal side abutment portion 32 toward the proximal direction. The depression dimension T is set to a size corresponding to a Young's modulus E of the proximal side transmitting member 15. The protruding dimension L of the projecting portion 25 and the depression dimension T of the depressed portion 33 are set as described above, so that a gap dimension (spatial dimension) D is defined between the protruding end 27 of the projecting portion 25 and the bottom portion 36 of the depressed portion 33 in the directions parallel to the longitudinal axis C. The size of the gap dimension D is set so that the ultrasonic transmitting unit 3 vibrates at the predetermined resonance frequency f0. When the gap dimension D is not zero, a cavity portion (space portion) 39 is formed between the protruding end 27 of the projecting portion 25 and the bottom portion 36 of the depressed portion 33.

The reference antinode position A2, which is one of the antinode positions (A1 to A3) of the ultrasonic vibration, is located at the protruding end 27 of the projecting portion 25, at the bottom portion 36 of the depressed portion 33, or between the protruding end 27 and the bottom portion 36 (i.e., in the cavity portion 39). That is, the standard antinode position A2 is located to the proximal direction side with respect to the proximal side abutment portion 32. The reference antinode position A2 is a proximate antinode position closest to the midway position M among the antinode positions (A1 to A3).

A manufacturing method of the ultrasonic transmitting unit 3 is now described. FIG. 5 is a diagram illustrating the manufacturing method of the ultrasonic transmitting unit 3. As shown in FIG. 5, in the manufacture of the ultrasonic transmitting unit 3, the ultrasonic vibrator 12 which is the vibration generating portion is formed (step S101). In parallel with the formation of the ultrasonic vibrator 12, the proximal side transmitting member 15 is formed (step S102), and the distal side transmitting member (ultrasonic probe) 21 is formed (step S103). The ultrasonic vibrator 12 is then attached to the rod portion 16 of the proximal side transmitting member 15 (step S104). The distal side transmitting member 21 is then attached to the distal direction side of the proximal side transmitting member 15 (step S105). In this way, the ultrasonic transmitting unit 3 is manufactured.

Figure 7:
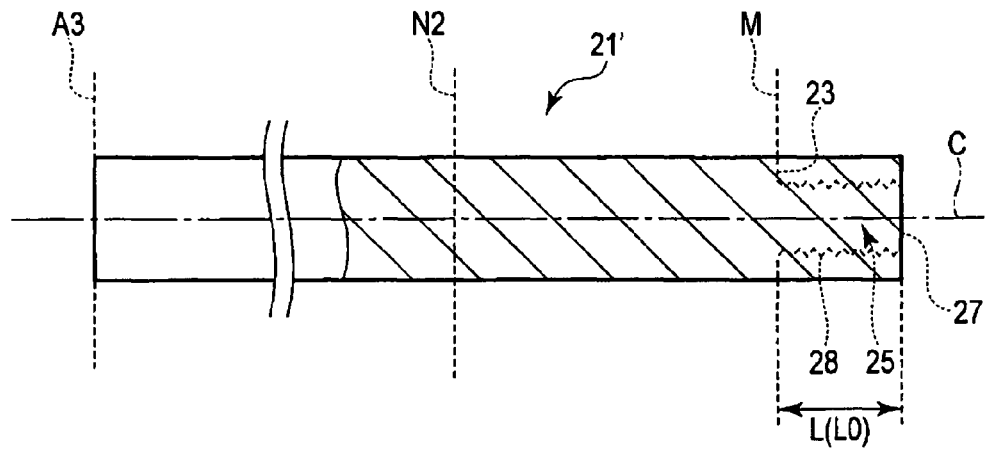
FIG. 7 is a schematic diagram showing a distal side preparatory member formed into the distal side transmitting member according to the first embodiment.

FIG. 6 is a diagram illustrating a method of forming the distal side transmitting member 21. FIG. 7 is a diagram showing a distal side preparatory member 21' formed into the distal side transmitting member 21. As shown in FIG. 6 and FIG. 7, the distal side transmitting member 21 is formed from the columnar distal side preparatory body 21'. In the present embodiment, the distal side preparatory member 21' is made of 64 titanium. In the formation of the distal side transmitting member 21, the distal side abutment portion 23 is formed in the distal side preparatory body 21' (step S111). The distal side abutment portion 23 is formed at the midway position M different from the antinode positions (A1 to A3) and the node positions (N1 and N2) of the ultrasonic vibration. That is, as shown in FIG. 3, the distal side abutment portion 23 is formed to be located at the position (midway position M) different from the antinode positions (A1 to A3) and the node positions (N1 and N2) of the ultrasonic vibration when the distal side transmitting member 21 and the proximal side transmitting member 15 are connected to each other. The projecting portion 25 is then formed in the distal side preparatory member 21' (step S112). At the same time, the external thread portion 28 is formed on the outer peripheral portion of the projecting portion 25. The projecting portion 25 is formed to protrude from the distal side abutment portion 23 toward the proximal direction. As a result of the formation of the projecting portion 25, the protruding end 27 of the projecting portion 25 becomes the proximal end of the distal side transmitting member 21. The projecting portion 25 is formed so that the protruding end 27 is located the protruding dimension L apart from the distal side abutment portion 23 toward the proximal direction. The protruding dimension L of the projecting portion 25 is set at the same size L0 in all the distal side transmitting members 21 to be formed. The distal side abutment portion 23 and the projecting portion 25 are formed in the distal side preparatory material 21', for example, by cutting.

Figure 8:
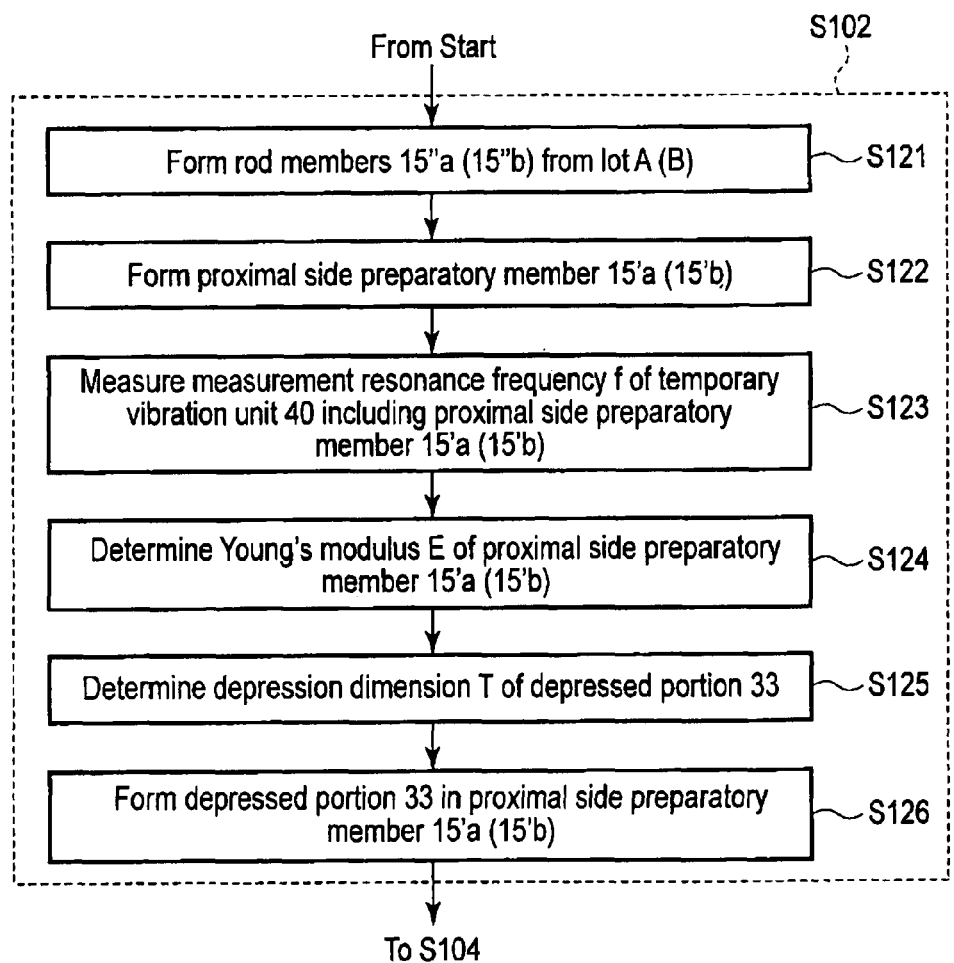
FIG. 8 is a flowchart showing a method of forming a proximal side transmitting member according to the first embodiment.

FIG. 8 and FIG. 9 are diagrams illustrating a method of forming the proximal side transmitting member 15. As shown in FIG. 8 and FIG. 9, the proximal side transmitting member 15 is formed from proximal side preparatory members 15'a and 15'b. The proximal side preparatory body 15'a is formed from columnar rod member 15"a, and the proximal side preparatory body 15'b is formed from columnar rod member 15"b. All the rod members 15"a are formed from a lot A, and all the rod members 15"b are formed from a lot B different from the lot A. In the present embodiment, the rod members 15"a and the rod members 15"b are made of 64 titanium. That is, the rod members 15"a of the lot A and the rod members 15"b of the lot B are made of a material of the same kind.

However, the lot A and the lot B are different, for example, in the content of aluminum in 64 titanium and in the ratio of β-phase titanium to α-phase titanium. The Young's modulus E of even 64 titanium, that is the same kind of the material, changes in accordance with the content of aluminum and the ratio of β-phase titanium to α-phase titanium. Therefore, the rod members 15"a formed from the lot A and the rod members 15"b formed from the lot B are different in the Young's modulus E. Although the formation of the proximal side transmitting member 15 from the lot A is described below, the proximal side transmitting member 15 is formed from the lot B in the same manner.

In the formation of the proximal side transmitting member 15, the rod members 15"a (rod members 15"b) are formed from the lot A (B) (step S121). The rod member 15"a (rod members 15"b) is then fabricated to form the proximal side preparatory member 15'a (15'b) (step S122). At the same time, the rod portion 16 and the horn 17 of the proximal side transmitting member 15 are formed. The proximal side abutment portion 32 is also formed at the distal end of the proximal side preparatory body 15'a (15'b).

All the proximal side preparatory members 15'a are formed into the same external shape. The proximal side preparatory member 15'a is formed into the same external shape as the proximal side preparatory member 15'b. Therefore, all the proximal side transmitting members 15 have the same external shape. The external shape of the proximal side transmitting member 15 (the proximal side preparatory members 15'a and 15'b) means the shape of the proximal side transmitting member 15 seen from the outside, and the shape of the depressed portion 33 is not included in the external shape of the proximal side transmitting member 15. The rod portion 16 and the horn 17 are formed, for example, by cutting.

In step S122, all the rod members 15"a (rod members 15"b) may be deformed into the proximal side preparatory members 15'a (15'b), or one of the rod members 15"a (15"b) may be selected and the selected rod member 15"a (15"b) alone may be deformed into the proximal side preparatory member 15'a (15'b).

A temporary vibration unit 40 including the proximal side preparatory member 15'a (15'b) is then formed, and a measurement resonance frequency f that is a frequency at which the temporary vibration unit 40 vibrates by the ultrasonic vibration is measured (step S123). FIG. 10A is a diagram showing a temporary vibration unit 40 according to a certain example. The temporary vibration unit 40 according to the present example is formed by attaching the ultrasonic vibrator 12 which is the vibration generating portion to the rod portion 16 of the proximal side preparatory member 15'a (15'b). The ultrasonic vibration is then generated by the ultrasonic vibrator 12. The measurement resonance frequency f of the temporary vibration unit 40 is measured by the use of the ultrasonic vibration generated by the ultrasonic vibrator 12.

FIG. 10B is a diagram showing a temporary vibration unit 40 according to another certain example. In the present example, a temporary depressed portion 33' is formed in the proximal side preparatory member 15'a (15'b). The temporary concave portion 33' is formed to be depressed from the proximal side abutment portion 32 toward the proximal direction. The temporary depressed portion 33' includes a temporary side portion 35' and a temporary bottom portion 36'. The temporary bottom portion 36' of the temporary depressed portion 33' is located a temporary depression dimension T' smaller than the depression dimension T of the depressed portion 33 apart from the proximal side abutment portion 32 toward the proximal direction. The temporary depression dimension T' of the temporary depressed portion 33' may be smaller than the protruding dimension L of the projecting portion 25. The temporary depressed portion 33' is formed in the proximal side preparatory member 15'a (15'b), for example, by cutting.

A vibration generator 41 is then attached to the proximal side preparatory member 15'a (15'b) via the temporary depressed portion 33'. The vibration generator 41 includes an external thread portion 42. The external thread portion 42 is screwed to an internal thread portion 43 provided in the temporary side portion 35' of the temporary depressed portion 33', and the vibration generator 41 is thereby attached to the proximal side preparatory member 15'a (15'b). When the vibration generator 41 is attached to the proximal side preparatory member 15'a (15'b), the temporary vibration unit 40 is formed. Here, the vibration generator 41 is separate from the ultrasonic vibrator (vibration generating portion) 12, and includes piezoelectric elements 45A to 45C. In the present example, an ultrasonic vibration is generated by the vibration generator 41 (the piezoelectric elements 45A to 45C). The measurement resonance frequency f of the temporary vibration unit 40 is measured by the use of the ultrasonic vibration generated by the vibration generator 41.

The Young's modulus E of the proximal side preparatory member 15'a (15'b) is then determined by the measured measurement resonance frequency f of the temporary vibration unit 40 (step S124). As described above, the Young's modulus E changes in accordance with, for example, the content of aluminum and the ratio of β-phase titanium to α-phase titanium, so that the rod members 15"a of the lot A and the rod members 15"b of the lot B are different in the Young's modulus E. Therefore, the proximal side preparatory member 15'a formed from the rod member 15"a and the proximal side preparatory member 15'b formed from the rod member 15"b are different in the Young's modulus E.

As described above, the proximal side preparatory member 15'a is formed into the same external shape as the proximal side preparatory member 15'b. Thus, the measurement resonance frequency f of the temporary vibration unit 40 changes in accordance with the Young's modulus E of the proximal side preparatory members (15'a and 15'b) included in the temporary vibration units 40. The proximal side preparatory member 15'a and the proximal side preparatory member 15'b are different in the Young's modulus E, so that in step S123, the measurement resonance frequency f is fa in the temporary vibration unit 40 including the proximal side preparatory member 15'a, and the measurement resonance frequency f is fb in the temporary vibration unit 40 including the proximal side preparatory member 15'b. Then in step S124, the Young's modulus E of the proximal side preparatory material 15'a is determined to be Ea by the value fa of the measurement resonance frequency f, and the Young's modulus E of the proximal side preparatory material 15'b is determined to be Eb by the value fb of the measurement resonance frequency f. In step S123 and step S124, it is only necessary to select one of the proximal side preparatory members 15'a (15'b), and measure the measurement resonance frequency f and determine Young's modulus E for the selected proximal side preparatory member 15'a (15'b) alone. In this case, the value Ea (Eb) of the Young's modulus E of the selected proximal side preparatory member 15'a (15'b) is determined as the Young's modulus E of all the proximal side preparatory members 15'a (15'b). The measurement resonance frequency f may be measured and the Young's modulus E may be determined for all the proximal side preparatory members 15'a (15'b).

The depression dimension T of the depressed portion 33 is determined by the Young's modulus E of the proximal side preparatory member 15'a (15'b) (step S125). The concave dimension T of the depressed portion 33 is determined within a range in which the depression dimension T is equal to or more than the protruding dimension L of the projecting portion 25. The depression dimension T of the depressed portion 33 is determined so that the ultrasonic transmitting unit 3 vibrates at the predetermined frequency f0.

FIG. 11 is a diagram showing the relation between the Young's modulus E of the proximal side preparatory members 15'a and 15'b (the proximal side transmitting member 15) and the depression dimension T of the depressed portion 33 in a situation in which the ultrasonic transmitting unit 3 vibrates at the predetermined frequency f0. In FIG. 11, a solid line indicates the case in which the kind of material of the proximal side transmitting member 15 is 64 titanium, and a broken line indicates the case in which the kind of material of the proximal side transmitting member 15 is duralumin. The relation between the Young's modulus E and the depression dimension T shown in FIG. 11 are determined in advance.

The resonance frequency of the ultrasonic vibration of the ultrasonic transmitting unit 3 is affected not only by the Young's modulus E of the proximal side transmitting member 15 but also by the size of the gap dimension D between the protruding end 27 of the projecting portion 25 and the bottom portion 36 of the depressed portion 33 in the directions parallel to the longitudinal axis C. As described above, the proximal side transmitting member 15 formed from proximal side preparatory member 15'a and the proximal side transmitting member 15 formed from proximal side preparatory member 15'b are different in the Young's modulus E. Thus, the size of the gap dimension D between the protruding end 27 of the projecting portion 25 and the bottom portion 36 of the depressed portion 33 is adjusted in accordance with the Young's modulus E of the proximal side preparatory member 15'a (15'b) (the measurement resonance frequency f of the temporary vibration unit 40) so that the ultrasonic transmitting unit 3 vibrates at the predetermined resonance frequency f0 regardless of the Young's modulus E of the proximal side preparatory member 15'a (15'b). As described above, the protruding dimension L of the projecting portion 25 is the same size L0 in all the distal side transmitting members 21. Therefore, the gap dimension D between the protruding end 27 of the projecting portion 25 and the bottom portion 36 of the depressed portion 33 is adjusted by the adjustment of the depression dimension T of the depressed portion 33 so that all the ultrasonic transmitting units 3 vibrate at the predetermined resonance frequency f0 regardless of the Young's modulus E of the proximal side preparatory member 15'a (15'b).

In the present embodiment, the proximal side preparatory members 15'a and 15'b are made of 64 titanium, so that the depression dimension T of the depressed portion 33 is determined by the relation indicated by the solid line in FIG. 11. The depression dimension T is determined to be Ta in the proximal side preparatory member 15'a in which the Young's modulus E is Ea. The depression dimension T is determined to be Tb in the proximal side preparatory member 15'b in which the Young's modulus E is Eb. As a result, the depression dimension T is determined so that the ultrasonic transmitting unit 3 vibrates at the predetermined frequency f0 both when the proximal side transmitting member 15 is formed from the proximal side preparatory member 15'a in which the Young's modulus E is Ea and when the proximal side transmitting member 15 is formed from the proximal side preparatory member 15'b in which the Young's modulus E is Eb.

The depressed portion 33 is then formed in the proximal side preparatory member 15'a (15'b) so that the bottom portion 36 is located the depression dimension T apart from the proximal side abutment portion 32 in the proximal direction (step S126). The proximal side transmitting member 15 is formed by the formation of the depressed portion 33. In the formation of the depressed portion 33, the internal thread portion 37 is formed on the side portion 35 of the depressed portion 33. In the example shown in FIG. 10A, the temporary depressed portion 33' is not provided in the proximal side preparatory member 15'a (15'b). Therefore, the depressed portion 33 depressed toward the proximal direction is formed in the proximal side abutment portion 32 which is formed into a flat shape from the longitudinal axis C to the outer peripheral end.

In the example shown in FIG. 10B, the temporary depressed portion 33' is formed in the proximal side preparatory member 15'a (15'b). Therefore, the depressed portion is formed by deforming the temporary depressed portion 33' on the basis of the Young's modulus E of the proximal side preparatory member 15'a (15'b). As described above, the temporary depression dimension T' of the temporary depressed portion 33' is smaller than the depression dimension T of the depressed portion 33. When the kind of material of the proximal side preparatory members (15'a and 15'b) is 64 titanium, the Young's modulus E of the proximal side preparatory members (15'a and 15'b) and the depression dimension T of the depressed portion 33 vary within the range of the solid line in FIG. 11. Therefore, the temporary depression dimension T' is smaller than a minimum value Tmin of the depression dimension T within the range of the variation. The ranges of the variations of the Young's modulus E and the depression dimension T are determined in advance. Since the temporary depression dimension T' of the temporary concave portion 33' is smaller than the depression dimension T of the depressed portion 33, the temporary depressed portion 33' can be deformed into the depressed portion 33.

In the present embodiment described, the kind of material of the proximal side transmitting member 15 is 64 titanium. However, when the kind of material of the proximal side transmitting member 15 is duralumin, the depression dimension T of the depressed portion 33 is determined by the relation indicated by the broken line in FIG. 11. The depressed portion 33 having the determined depression dimension T is then formed.

When the value Ea (Eb) of the Young's modulus E of the one proximal side preparatory member 15'a (15'b) selected in step S124 is determined as the Young's modulus E of all the proximal side preparatory members 15'a (15'b), the depression dimension T of the depressed portion 33 is the same size Ta (Tb) in all the proximal side preparatory members 15'a (15'b) in step S125 and step S126. On the other hand, when the Young's modulus E is determined for all the proximal side preparatory members 15'a (15'b) in step S124, the value of the Young's modulus E slightly differs according to the proximal side preparatory members 15'a (15'b). Therefore, the depression dimension T of the depressed portion 33 is adjusted for each of the proximal side preparatory members 15'a in accordance with the slight difference of the value of the Young's modulus between the proximal side preparatory members 15'a (15'b).

FIG. 12 is a diagram showing a method of attaching the distal side transmitting member 21 to the proximal side transmitting member 15. As shown in FIG. 12, in the attachment of the distal side transmitting member 21 to the proximal side transmitting member 15, the external thread portion 28 and the internal thread portion 37 are screwed together, and the projecting portion 25 is engaged with the depressed portion 33 (step S131). When the projecting portion 25 is engaged with the depressed portion 33, the distal side abutment portion 23 of the distal side transmitting member 21 abuts on the proximal side abutment portion 32 of the proximal side transmitting member 15 (step S132). As a result, the ultrasonic vibration can be transmitted to the distal side transmitting member 21 from the proximal side transmitting member 15. The distal side abutment portion 23 abuts on the proximal side abutment portion 32 at the midway position M different from the antinode positions (A1 to A3) and the node positions (N1 and N2) of the ultrasonic vibration.

The bottom portion 36 is located the depression dimension T apart from the proximal side abutment portion 32 toward the proximal direction in the depressed portion 33 with which the projecting portion 25 is engaged, and the depression dimension T of the depressed portion 33 is adjusted in step S125 as described above. Thus, when the projecting portion 25 is engaged with the depressed portion 33, the gap dimension D between the protruding end 27 of the projecting portion 25 and the bottom portion 36 of the depressed portion 33 in the directions parallel to the longitudinal axis C is set (step S133). The size of the gap dimension D is set so that the ultrasonic transmitting unit 3 vibrates at the predetermined resonance frequency f0.

The projecting portion 25 is engaged with the depressed portion 33 so that the reference antinode position A2 which is one of the antinode positions (A1 to A3) of the ultrasonic vibration is located at the protruding end 27 of the projecting portion 25, at the bottom portion 36 of the depressed portion 33, or between the protruding end 27 and the bottom portion 36 (i.e., in the cavity portion 39) (step S134). That is, the reference antinode position A2 is located to the proximal direction side with respect to the proximal side abutment portion 32.

Since the ultrasonic transmitting unit 3 is manufactured as described above, the depression dimension T of the depressed portion 33 can be adjusted in accordance with the degree of the Young's modulus E of the proximal side transmitting member 15 which varies according to the ultrasonic transmitting units 3. The protruding dimension L of the projecting portion 25 is the same size L0 in all the distal side transmitting members 21, so that the gap dimension D between the protruding end 27 of the projecting portion 25 and the bottom portion 36 of the depressed portion 33 in the directions parallel to the longitudinal axis C is adjusted by the adjustment of the depression dimension T of the depressed portion 33 of the proximal side transmitting member 15. The size of the gap dimension D that affects the resonance frequency of the ultrasonic vibration of the ultrasonic transmitting unit 3 is adjusted in accordance with the degree of the Young's modulus E of the proximal side transmitting member 15. Therefore, even when the Young's modulus E varies according to the proximal side transmitting members 15, all the ultrasonic transmitting units 3 can be set so that the ultrasonic transmitting units 3 vibrate at the predetermined resonance frequency f0. As a result, the variation of the resonance frequency of the ultrasonic vibration in the ultrasonic transmitting units 3 (products) to be manufactured can be effectively suppressed.

In the ultrasonic transmitting unit 3, the size of the depression dimension T of the depressed portion 33 is adjusted for each of the proximal side transmitting members 15 in accordance with the degree of the Young's modulus E of the proximal side transmitting member 15. That is, the external shape of each of the proximal side transmitting members 15 is not changed in accordance with the degree of the Young's modulus E of the proximal side transmitting member 15. Thus, costs and time are reduced in the manufacture of the ultrasonic transmitting unit 3. Therefore, the ultrasonic transmitting unit 3 can be easily manufactured even when the degree of the Young's modulus E varies according to the proximal side transmitting members 15.

Now, the functions of the ultrasonic transmitting unit 3 are described. When a treatment target such as a living tissue is treated by the use of the ultrasonic transmitting unit 3, an electric current is supplied to the ultrasonic vibrator 12 from the electric current supply section 7 via the electric wiring lines 13A and 13B by the operation in the input section 9. As a result, an ultrasonic vibration is generated in the ultrasonic vibrator 12, and the ultrasonic vibration is transmitted to the distal side transmitting member 21, which is an ultrasonic probe, through the proximal side transmitting member 15. When the ultrasonic vibration is transmitted from the proximal direction toward the distal direction, the ultrasonic transmitting unit 3 vibrates at the predetermined resonance frequency f0. While the ultrasonic transmitting unit 3 is vibrating, the distal portion of the distal side transmitting member 21 treats the treatment target.

Here, when the gap dimension D is not zero, the cavity portion 39 is formed between the protruding end 27 of the projecting portion 25 and the bottom portion 36 of the depressed portion 33. The sectional shape of the ultrasonic transmitting unit 3 perpendicular to the longitudinal axis C through the cavity portion 39 is cylindrical (hollow). In contrast, the sectional shape of the ultrasonic transmitting unit 3 perpendicular to the longitudinal axis C through parts other than the cavity portion 39 is columnar (solid). That is, the cavity portion 39 is provided so that the sectional shape of the ultrasonic transmitting unit 3 perpendicular to the longitudinal axis C greatly changes from the columnar shape to the cylindrical shape in the bottom portion 36 of the depressed portion 33 and so that the sectional shape of the ultrasonic transmitting unit 3 perpendicular to the longitudinal axis C greatly changes from the cylindrical shape to the columnar shape in the protruding end 27 of the projecting portion 25. At the position where the sectional shape of the ultrasonic transmitting unit 3 perpendicular to the transmission direction and the vibration direction of the ultrasonic vibration greatly changes, the ultrasonic vibration tends to be affected by stress in directions perpendicular to the longitudinal axis C. If the ultrasonic vibration is affected by the stress, the vibration mode of the ultrasonic vibration changes, and the ultrasonic vibration may not be properly transmitted to the distal end of the ultrasonic transmitting unit 3 (the distal portion of the distal side transmitting member 21).

Thus, in the ultrasonic transmitting unit 3, the standard antinode position A2 which is one of the antinode positions (A1 to A3) of the ultrasonic vibration is located at the protruding end 27 of the projecting portion 25, at the bottom portion 36 of the depressed portion 33, or between the protruding end 27 and the bottom portion 36 (i.e. in the cavity portion 39). Therefore, the protruding end 27 of the projecting portion 25 and the bottom portion 36 of the depressed portion 33 in which the sectional shape of the ultrasonic transmitting unit 3 perpendicular to the transmission direction and the vibration direction of the ultrasonic vibration greatly changes are located in the vicinity of the reference antinode position A2. At the antinode positions (A1 to A3) of the ultrasonic vibration including the reference antinode position A2, the amplitude is at the maximum, but the stress in the directions perpendicular to the longitudinal axis C is zero. Therefore, the stress in the directions perpendicular to the longitudinal axis C is low in the protruding end 27 of the projecting portion 25 and the bottom portion 36 of the depressed portion 33 that are located in the vicinity of the reference antinode position A2. Thus, in the protruding end 27 of the projecting portion 25 and the bottom portion 36 of the depressed portion 33 in which the sectional shape of the ultrasonic transmitting unit 3 perpendicular to the transmission direction and the vibration direction of the ultrasonic vibration greatly changes, the ultrasonic vibration is hardly affected by the stress in the directions perpendicular to the longitudinal axis C. Therefore, even when the cavity portion 39 is provided, the change of the vibration mode of the ultrasonic vibration is suppressed, and the ultrasonic vibration can be properly transmitted to the distal end of the ultrasonic transmitting unit 3 (the distal portion of the distal side transmitting member 21).

(Modifications)

Figure 13:
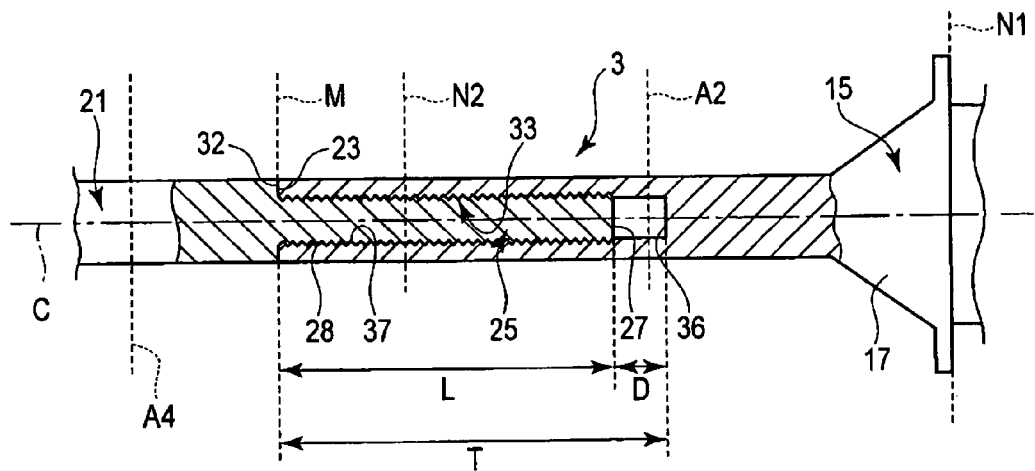
FIG. 13 is a schematic diagram showing the configuration of an ultrasonic transmitting unit according to a first modification.

In the first embodiment, the reference antinode position A2 which is located at the protruding end 27 of the projecting portion 25, at the bottom portion 36 of the depressed portion 33, or between the protruding end 27 and the bottom portion 36 (i.e., in the cavity portion 39) is the proximate antinode position closest to the midway position M among the antinode positions (A1 to A3) of the ultrasonic vibration. However, this is not a limitation. For example, as in a first modification shown in FIG. 13, the reference loop position A2 which is located at the protruding end 27 of the projecting portion 25, at the bottom portion 36 of the depressed portion 33, or between the protruding end 27 and the bottom portion 36 (i.e., in the cavity portion 39) may be different from a proximate antinode position A4. That is, the reference antinode position A2 is located to the proximal direction side with respect to the proximate antinode position A4 which is closest to the midway position M among the antinode positions (A1 to A4) of the ultrasonic vibration.

In the present modification, the protruding end 27 of the projecting portion 25 is located to the proximal direction side with respect to the proximate antinode position A4. The bottom portion 36 of the depressed portion 33 is located to the proximal direction side with respect to the proximate antinode position A4. In the present modification as well, the gap dimension D between the protruding end 27 of the projecting portion 25 and the bottom portion 36 of the depressed portion 33 is adjusted so that the ultrasonic transmitting unit 3 vibrates at the predetermined frequency f0.

Figure 14:
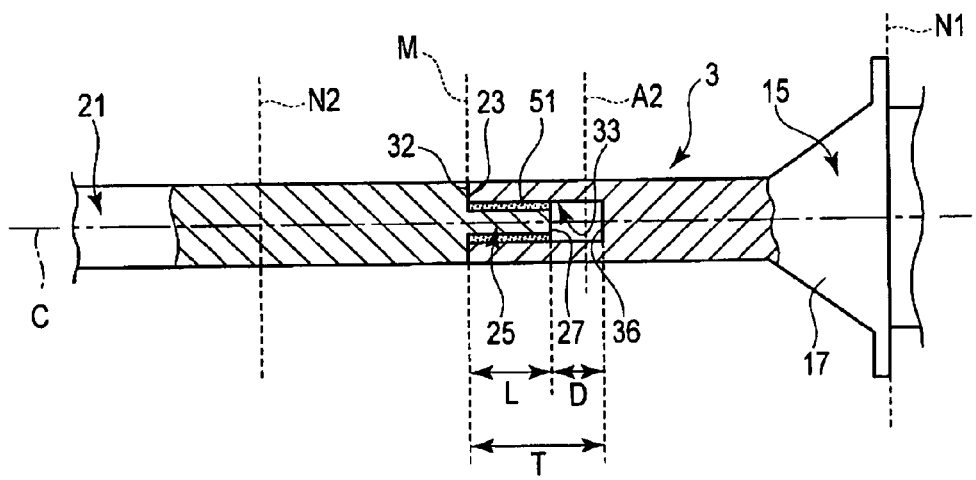
FIG. 14 is a schematic diagram showing the configuration of an ultrasonic transmitting unit according to a second modification.

In the first embodiment, the external thread portion 28 of the projecting portion 25 is screwed to the internal thread portion 37, and the projecting portion 25 is thereby engaged with the depressed portion 33. However, this is not a limitation. For example, as in a second modification shown in FIG. 14, the outer peripheral portion of the projecting portion 25 and the side portion 35 of the depressed portion 33 may be joined together by a jointing material 51. When the outer circumferential portion of the projecting portion 25 and the side portion 35 of the depressed portion 33 are joined together, the projecting portion 25 is engaged with the depressed portion 33.

In the present modification as well, the distal side abutment portion 23 abuts on the proximal side abutment portion 32. The gap dimension D between the protruding end 27 of the projecting portion 25 and the bottom portion 36 of the depressed portion 33 is adjusted so that the ultrasonic transmitting unit 3 vibrates at the predetermined frequency f0.

According to the modifications described above, the distal side transmitting member 21 has only to include the distal side abutment portion 23 located at the midway position M different from the antinode positions (A1 to A3; A1 to A4) and the node positions (N1 and N2) of the ultrasonic vibration, and the projecting portion 25 provided to protrude from the distal side abutment portion 23 toward the proximal direction. The protruding end 27 of the projecting portion 25 has only to be located at the proximal end of the distal side transmitting member 21, and located the protruding dimension L (L0) apart from the distal side abutment portion 23 toward the proximal direction. The proximal side transmitting member 15 has only to include the proximal side abutment portion 32 which is provided at the distal end of the proximal side transmitting member 15 and which abuts on the distal side abutment portion 23, and the depressed portion 33 which is provided to be depressed from the proximal side abutment portion 32 toward the proximal direction and with which the projecting portion 25 is engaged. The bottom portion 36 of the depressed portion 33 has only to be located apart from the proximal side abutment portion 32 toward the proximal direction by the depression dimension T which is equal to or more than the protruding dimension L and which is set to the size corresponding to the Young's modulus E of the proximal side transmitting member 15. Consequently, the size of the gap dimension D between the protruding end 27 of the projecting portion 25 and the bottom portion 36 of the depressed portion 33 in the directions parallel to the longitudinal axis C is set so that the ultrasonic transmitting unit 3 vibrates at the predetermined resonance frequency f0.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic transmitting unit which extends along a longitudinal axis and which is configured to transmit an ultrasonic vibration from a proximal direction toward a distal direction and thereby configured to vibrate at a predetermined resonance frequency, the ultrasonic transmitting unit comprising:

a vibration generating portion which is configured to generate the ultrasonic vibration;

a proximal side transmitting member to which the vibration generating portion is attached and to which the ultrasonic vibration is configured to be transmitted from the vibration generating portion, the proximal side transmitting member including a proximal side abutment portion which forms a distal end of the proximal side transmitting member;

a distal side transmitting member connected to the proximal side transmitting member to which the ultrasonic vibration is transmitted from the vibration generating portion, the distal side transmitting member including a distal side abutment portion on which the proximal side abutment portion of the proximal side transmitting member abuts when the distal side transmitting member is connected to the proximal side transmitting member;

a projecting portion protruding from the distal side abutment portion toward the proximal direction in the distal side transmitting member, the projecting portion including a protruding end located a predetermined protruding dimension apart from the distal side abutment portion; and a depressed portion which is depressed from the proximal side abutment portion toward the proximal direction and which includes a bottom portion spaced a depression dimension equal to or more than the predetermined protruding dimension apart from the proximal side transmitting member, the depressed dimension being set in accordance with a Young's modulus of the proximal side transmitting member based on a relation between the Young's modulus of the proximal side transmitting member and the depression dimension so that the proximal side transmitting member and the distal side transmitting member vibrates at the predetermined resonance frequency where an antinode position of the ultrasonic vibration is located within a range in which a cavity portion formed between the protruding end of the projecting portion and the bottom portion of the depressed portion in a situation in which the ultrasonic transmitting unit transmits the ultrasonic vibration.

2. The ultrasonic transmitting unit according to claim 1, wherein
in the situation in which the ultrasonic transmitting unit vibrates at the predetermined resonance frequency, the proximal side abutment portion and the distal side abutment portion are located at positions different from the antinode positions and node positions of the ultrasonic vibration, and a reference antinode position which is an antinode position located between the protruding end of the projecting portion and the bottom portion of the depressed portion in the situation in which the ultrasonic transmitting unit vibrates at the predetermined resonance frequency is a proximate antinode position closest to the proximal side abutment portion and the distal side abutment portion among the antinode positions of the ultrasonic vibration.

3. The ultrasonic transmitting unit according to claim 1, wherein the proximal side transmitting member includes a horn which is configured to increase the amplitude of the ultrasonic vibration.

4. The ultrasonic transmitting unit according to claim 1, wherein
the projecting portion includes an external thread portion, and
the depressed portion includes an internal thread portion which is screwed to the external thread portion to engage the projecting portion with the depressed portion.

5. A manufacturing method of an ultrasonic transmitting unit which extends along a longitudinal axis and which is configured to transmit an ultrasonic vibration from a proximal direction toward a distal direction and thereby configured to vibrate at a predetermined resonance frequency, the manufacturing method comprising:
forming a vibration generating portion which is configure to generate the ultrasonic vibration;
forming a proximal side transmitting member to which the ultrasonic vibration is configured to be transmitted from the vibration generating portion and forming a distal end of the proximal side transmitting member by a proximal side abutment portion;
attaching the vibration generating portion to the proximal side transmitting member;
forming a distal side transmitting member to which the ultrasonic vibration is configured to be transmitted from the proximal side transmitting member;
connecting the distal side transmitting member to the distal direction side of the proximal side transmitting member so that the proximal side abutment portion of the proximal side transmitting member abuts on a distal side abutment portion of the distal side transmitting member;
forming a projecting portion protruding from the distal side abutment portion toward the proximal direction in the distal side transmitting member, and forming a proximal end of the distal side transmitting member by a protruding end of the projecting portion which is located a predetermined protruding dimension apart from the distal side abutment portion toward the proximal direction;
forming a depressed portion which is depressed from the proximal side abutment portion toward the proximal direction in the proximal side transmitting member, setting a depression dimension equal to or more than the predetermined protruding dimension from the proximal side abutment portion to a bottom portion of the depressed portion accordance with a Young's modulus of the proximal side transmitting member based on a relation between the Young's modulus of the proximal side transmitting member and the depression dimension, and then forming the depressed portion having the set depression dimension from the proximal side abutment portion to the bottom portion;
forming a cavity portion having a space between the protruding end of the projecting portion and the bottom portion of the depressed portion inside the proximal side transmitting member when the distal side transmitting member is connected to the proximal side transmitting member and then the depressed portion is engaged with the projecting portion; and
connecting the distal side transmitting member to the proximal side transmitting member in which the depression dimension is set so that the proximal side transmitting member and the distal side transmitting member vibrates at the predetermined resonance frequency where an antinode position of the ultrasonic vibration is located within a range in which the cavity portion is formed between the protruding end of the projecting portion and the bottom portion of the depressed portion when the ultrasonic transmitting unit transmits the ultrasonic vibration.

6. The manufacturing method according to claim 5, wherein forming the depressed portion in the proximal side transmitting member includes
measuring a measurement resonance frequency that is a resonance frequency at which a temporary vibration unit including the proximal side transmitting member vibrates by the ultrasonic vibration, and determining the Young's modulus of the proximal side transmitting member based on the measured measurement resonance frequency.

7. The manufacturing method according to claim 6, wherein measuring the measurement resonance frequency of the temporary vibration unit includes
attaching the vibration generating portion to the proximal side transmitting member to form the temporary vibration unit, and
generating the ultrasonic vibration by the vibration generating portion.

8. The manufacturing method according to claim 6, wherein measuring the measurement resonance frequency of the temporary vibration unit includes
forming a temporary depressed portion which is depressed from the proximal side abutment portion toward the proximal direction in the proximal side transmitting member, and locating a temporary bottom portion of the temporary depressed portion a temporary depression dimension smaller than the depression dimension of the depressed portion apart from the proximal side abutment portion toward the proximal direction,
attaching a vibration generator separate from the vibration generating portion to the proximal side transmitting member via the temporary depressed portion to form the temporary vibration unit, and
generating the ultrasonic vibration by the vibration generator, and
forming the depressed portion in the proximal side transmitting member includes deforming the temporary depressed portion on the basis of the Young's modulus of the proximal side transmitting member.

9. The manufacturing method according to claim 8, wherein forming the temporary depressed portion includes forming the temporary depressed portion so that the temporary depression dimension is smaller than the predetermined protruding dimension of the projecting portion.

* * * * *